United States Patent [19]
Deeley et al.

[11] Patent Number: 5,405,952
[45] Date of Patent: Apr. 11, 1995

[54] DNA SEQUENCE ENCODING NONGLYCOSYLATED ANALOGS OF HUMAN COLONY STIMULATING FACTORS

[75] Inventors: Michael Deeley, Edmonds; Virginia L. Price; David Urdal, both of Seattle, all of Wash.

[73] Assignee: Immunex Corporation, Seattle, Wash.

[21] Appl. No.: 262,385

[22] Filed: Oct. 24, 1988

Related U.S. Application Data

[62] Division of Ser. No. 918,428, Oct. 14, 1986.

[51] Int. Cl.$^6$ .................. C07H 15/12; C12P 21/02; C12P 19/34; C12N 15/00; C12N 7/00; C12N 1/21; C12N 1/16; C12N 1/18; C07K 3/00
[52] U.S. Cl. .................. 536/23.5; 435/69.5; 435/69.9; 435/172.3; 435/320.1; 435/235.1; 435/252.3; 530/350; 935/10; 935/28; 935/56; 935/61; 935/69
[58] Field of Search .............. 435/69.9, 91, 172.3, 435/256, 320, 940, 320.1, 235.1, 252.33, 255, 69.5; 536/27; 530/358; 935/10, 28, 41, 56, 61, 69, 81

[56] References Cited

U.S. PATENT DOCUMENTS

| | | | |
|---|---|---|---|
| 4,546,082 | 10/1985 | Kurjan et al. | 435/172.3 |
| 4,876,197 | 10/1989 | Burke et al. | 435/172.3 |
| 4,877,729 | 10/1989 | Clark et al. | 435/68 |

OTHER PUBLICATIONS

Cantrell et al., "Cloning, Sequence, and Expression of a Human Granulocyte/Macrophage Colony Stimulating Factor," *Proc. Natl. Acad. Sci.* 82:6250 (1985).
Wong et al., "Human GM-CSF: Molecular Cloning of the Complementary DNA and Purification of the Natural and Recombinant Proteins," *Science* 228:810 (1985).
Lee et al., "Isolation of cDNA for a Human Granulocyte-Macrophage Colony Stimulating Factor by Functional Expression in Mammalian Cells," *Proc. Natl. Acad. Sci.* 82:4360 (1985).
Miyajima et al., "Expression of Murine and Human Granulocyte Macrophage Colony Stimulating Factors in *S. cerevisiae*: Mutagenesis of the Potential Glycosylation Sites," *EMBO* 5:1193 (1986).
Kawasaki et al., "Molecular Cloning of a Complementary DNA Encoding Human Macrophage Specific Colony Stimulating Factor (CSF-1)," *Science* 230:291 (1985).
Gasson et al., "Molecular Characterization and Expression of the Gene Encoding Human Erythroid-Potentiating Activity," *Nature* 315:768 (1985).
Yang et al., "Human IL-3 (Multi-CSF): Identification by Expression Cloning of a Novel Hematopoietic Growth Factor Related to Murine IL-3," *Cell* 47:3 (1986).
Donahue, et al Cold Spring Harbor Symposia on Quantitative Biology, vol. LI, CSH Laboratory, N.Y. (1986) (Meeting Date-Jun. 1986).
Valenzuela et al Nature vol. 298 pp. 347-350 (1982).

*Primary Examiner*—Joan Ellis
*Attorney, Agent, or Firm*—Foley & Lardner

[57] ABSTRACT

An analog human colony stimulating factor (hCSF) is disclosed, comprising a mutant amino acid sequence which is substantially homologous to the native sequence of an hCSF having at least one N-glycosylation site, wherein the mutant sequence comprises at least one amino acid substitution, deletion or insertion inactivating the N-glycosylation site.

1 Claim, 4 Drawing Sheets

FIG. 2

```
GCA CCC GCC CGC TCG CCC AGC ACA CAG CCC TGG GAA CAT   45
Ala Pro Ala Arg Ser Pro Ser Thr Gln Pro Trp Glu His   15

GTG AAT GCC ATC CAG GAA GCC CGT CTC AAC CTG AGT AGA   90
Val Asn Ala Ile Gln Glu Ala Arg Arg Leu Asn Leu Ser Arg   30

GAC ACT GCT GAG ATG AAT GAA ACA GTA GAA ATC TCA GAA  135
Asp Thr Ala Glu Met Asn Glu Thr Val Glu Ile Ser Glu   45

ATG TTT GAC CTC CAG GAG CCG ACC TGC CTA CAG ACC CTG GAG  180
Met Phe Asp Leu Gln Glu Pro Thr Cys Leu Gln Thr Arg Leu Glu   60

CTG TAC AAG CAG GGC CTG CGG AGC CTC ACC AAG CTC AAG GGC  225
Leu Tyr Lys Gln Gly Leu Arg Ser Leu Thr Lys Leu Lys Gly   75

CCC TTG ACC ATG ATG GCC AGC CAC TAC AAA CAG CAC TGC CCA  270
Pro Leu Thr Met Met Ala Ser His Tyr Lys Gln His Cys Pro Pro   90

ACC CCG GAA ACT TCC TGT GCA ACC CAG ATT ATC TTT GAA AGT  315
Thr Pro Glu Thr Ser Cys Ala Thr Gln Ile Ile Phe Glu Ser  105

TTC AAA GAG AAC CTG AAG GAC TTT CTG CTT GTC ATC CCC TTT GAC  360
Phe Lys Glu Asn Leu Lys Asp Phe Leu Leu Val Ile Pro Phe Asp  120

TGC TGG GAG CCA AAG CAG GAG TGA GAG CGG CCA GAT GAG GCT GGC  405
Cys Trp Lys Pro Val Gln Glu End                             127

CAA GCC GGG GAG CTG CTC TCT CAT GAA ACA AGA GCT AGA AAC TCA  450

GGA TGG TCA TCT TGG AGG GAC CAA GGG GTG GGC CAC AGC CAT GGT  495
```

FIG. 3

```
  G GTA CCT TTG GAT AAA AGA
    Val Pro Leu Asp Lys Arg

GCT CCA GCT AGA TCT CCA TCT ACT CAA CCA TGG GAA CAC            45
Ala Pro Ala Arg Ser Pro Ser Thr Gln Pro Trp Glu His            15

GTT AAC GCT ATT CAA GAA GCT TTG CGT CTC CTG GAC AGT AGA        90
Val Asn Ala Ile Gln Glu Ala Leu Arg Leu Leu Asp Ser Arg        30

GAC ACT GCT GCT GAG ATG AAT GAA GTA GAA GTC ATC TCA GAA       135
Asp Thr Ala Ala Glu Met Asn Glu Val Glu Val Ile Ser Glu        45

ATG TTT GAC CTC CAG GAG CCG ACC TGC CTA CAG ACC CTG GAG       180
Met Phe Asp Leu Gln Glu Pro Thr Cys Leu Gln Thr Leu Glu        60

CTG TAC AAG CAG GGC CTG CGG AGC CTC ACC AAG CTC AAG GGC       225
Leu Tyr Lys Gln Gly Leu Arg Ser Leu Thr Lys Leu Lys Gly        75

CCC TTG ACC ATG ATG GCC CAC CAC TAC AAG CAG TGC CCT CCA       270
Pro Leu Thr Met Met Ala Ser His Tyr Lys Gln His Cys Pro Pro    90

ACC CCG GAA ACT TCC TGT GCA ACC CAG ATT ATC ACC TTT GAA AGT   315
Thr Pro Glu Thr Ser Cys Ala Thr Gln Ile Ile Thr Phe Glu Ser   105

TTC AAA GAG AAC CTG AAG GAC TTT CTG CTT GTC ATC CCC TTT GAC   360
Phe Lys Glu Asn Leu Lys Asp Phe Leu Leu Val Ile Pro Phe Asp   120

TGC TGG AAG CCA GTC CAG GAG TGA GAC CGG CCA GAT GAG GCT GGC   405
Cys Trp Lys Pro Val Gln Glu End                               127

CAA GCC GGG GAG CTG CTC TCT CAT GAA ACA AGA GCT AGA AAC TCA   450

GGA TGG TCA TCT TGG AGG GAC CAA GGG GTG GGC CAC AGC CAT GGT   495
```

DNA SEQUENCE ENCODING NONGLYCOSYLATED ANALOGS OF HUMAN COLONY STIMULATING FACTORS

This application is a division of application Ser. No. 918,428, filed Oct. 14, 1986.

BACKGROUND OF THE INVENTION

The present invention relates generally to analogs of endogenous glycoproteins, and particularly to analogs of secreted proteins capable of inducing hematopoetic cell development.

Many proteins secreted by cells into the extracellular environment acquire covalently attached carbohydrate units following translation, typically in the form of oligosaccharide units linked to asparagine side chains by N-glycosidic bonds. Both the structure and number of oligosaccharide units attached to a particular secreted protein can be highly variable, resulting in a wide range of apparent molecular masses attributable to a single glycoprotein. Many regulatory proteins having potential utility as human and veterinary therapeutic agents are secreted glycoproteins of this type. Attempts to express such proteins in recombinant systems have been complicated by the heterogeneity attributable to this variable carbohydrate component.

Immunoregulatory proteins, or lymphokines, are a class of secreted proteins; many are glycoproteins. For example, growth and differentiation of hematopoeitic cells is mediated by a number of glycoproteins collectively referred to as colony stimulating factors or CSFs. In humans, these proteins include granulocyte-macrophage colony stimulating factor (GM-CSF), a glycoprotein required for the production of granulocytes and macrophages from normal bone marrow which also appears to regulate the activity of mature, differentiated granulocytes and macrophages. Other human CSFs (hCSFs) include macrophage CSF (M-CSF-or CSF-1), which induces the selective proliferation of macrophages, granulocyte CSF (G-CSF), which stimulates development of granulocytes, and burst promoting activity (BPA), which induces development of erythroid cell progenitors into hemoglobin-containing cells. An additional murine CSF, known variously as IL-3 or multi-CSF, stimulates the development of numerous cell types of hematopoeitic lineage. A human homologue of murine IL-3 has recently been reported.

GM-CSF was initially identified as a 23 kilodalton protein present in preparations obtained from endotoxin-conditioned mouse lung. See Burgess et al., *J. Biol. Chem.* 252:1998 (1977). Human GM-CSF activity was partially purified from placental conditioned medium by Nicola et al., *Blood* 54:614 (1979). Human GM-CSF has also been identified in cultures of the human T-lymphoblast cell line Mo, and shown to modulate the activities of mature neutrophilic granulocytes by Gasson et al., *Science* 226:1339 (1984). Cloning and expression of recombinant human GM-CSF from various sources has been reported by Cantrell et al., *Proc. Natl. Acad. Sci. USA* 82:6250 (1985); Wong et al., *Science* 228:810 (1985); and Lee et al., *Proc. Natl. Acad. Sci. USA* 82:4360 (1985). Cantrell et al. isolated human GM-CSF sequences from cDNA libraries prepared from the HUT-102 cell line. The isolated human sequences were shown to direct synthesis of a biologically active GM-CSF using a yeast expression system.

Recombinant proteins which are expressed, glycosylated and secreted by yeast typically contain variable quantities of associated carbohydrate. Thus, purified mixtures of recombinant glycoproteins such as human or murine GM-CSF can consist of from 0 to 50% carbohydrate by weight. Miyajima et al., *EMBO Journal* 5:1193 (1986) reported expression of a recombinant murine GM-CSF in which N-glycosylation sites had been mutated to preclude glycosylation and reduce heterogeneity of the yeast-expressed product.

The presence of variable quantities of associated carbohydrate in recombinant secreted glycoproteins complicates purification procedures, thereby reducing yield. In addition, should the glycoprotein be employed as a therapeutic agent, a possibility exists that recipients will develop allergic reactions to the yeast carbohydrate moities, requiring therapy to be discontinued. For these reasons, biologically active, homogeneous analogs of immunoregulatory glycoproteins having reduced carbohydrate are desirable for therapeutic use.

It has now been found that functional mutant analogs of human GM-CSF and other human CSFs normally secreted as glycoproteins can be produced by site-specific mutagenesis techniques. These analog proteins can be produced in a homogeneous, reduced-carbohydrate form in higher yields than wild-type homologues, using yeast expression systems. The reduced-carbohydrate analogs of human GM-CSF exhibit a specific activity equivalent to comparable purified mixtures of glycosylated recombinant human GM-CSF in appropriate assays of colony-stimulating activity.

SUMMARY OF THE INVENTION

The present invention provides an analog human colony simulating factor (hCSF) comprising a mutant amino acid sequence which is substantially homologous to the native sequence of an hCSF having at least one N-glycosylation site, wherein the mutant sequence comprises at least one amino acid substitution, deletion, or insertion inactivating the N-glycosylation site. In related aspects, the invention provides recombinant DNA segments comprising nucleotide sequences encoding the analog hCSFs, and recombinant expression systems comprising the DNA segments.

BRIEF DESCRIPTION OF THE DRAWINGS

FIG. 2 depicts the nucleotide sequence and corresponding amino acid sequence of the wild type human GM-CSF gene.

FIG. 3 depicts the nucleotide sequence and corresponding amino acid sequence of a DNA segment encoding a mutant analog human GM-CSF, hGM-CSF[Leu$^{23}$Asp$^{27}$Glu$^{39}$].

DETAILED DESCRIPTION OF THE INVENTION

Figure 1A:
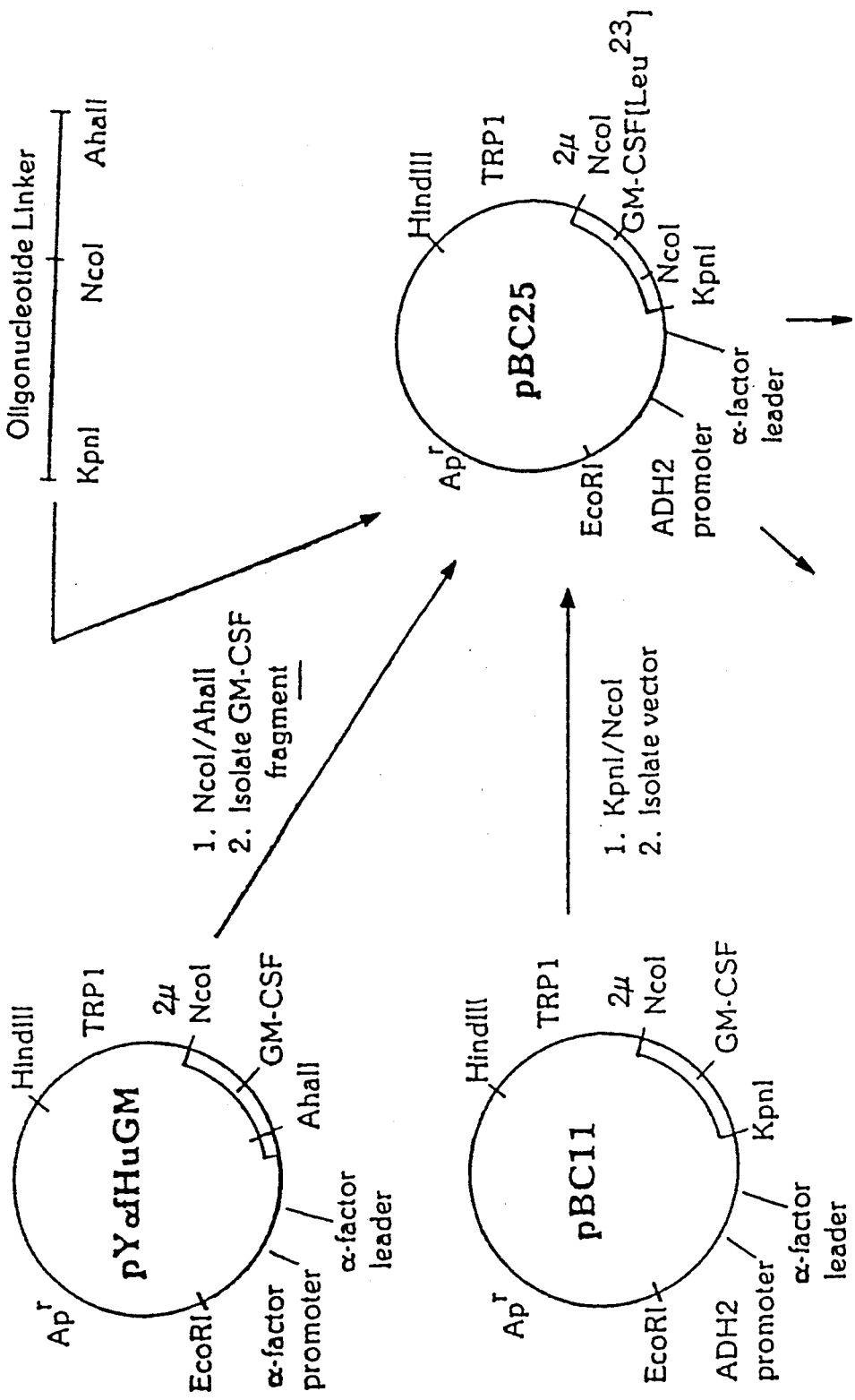
FIG. 1 is a schematic representation of the assembly of a yeast expression vector, designated pαADH-2HuGMCSFLeu$^{23}$Asp$^{27}$Glu$^{39}$ (L207-5, ATCC 67,231), which comprises a coding sequence for a reduced-carbohydrate form of human granulocyte-macrophage colony stimulating factor.
Figure 1B:
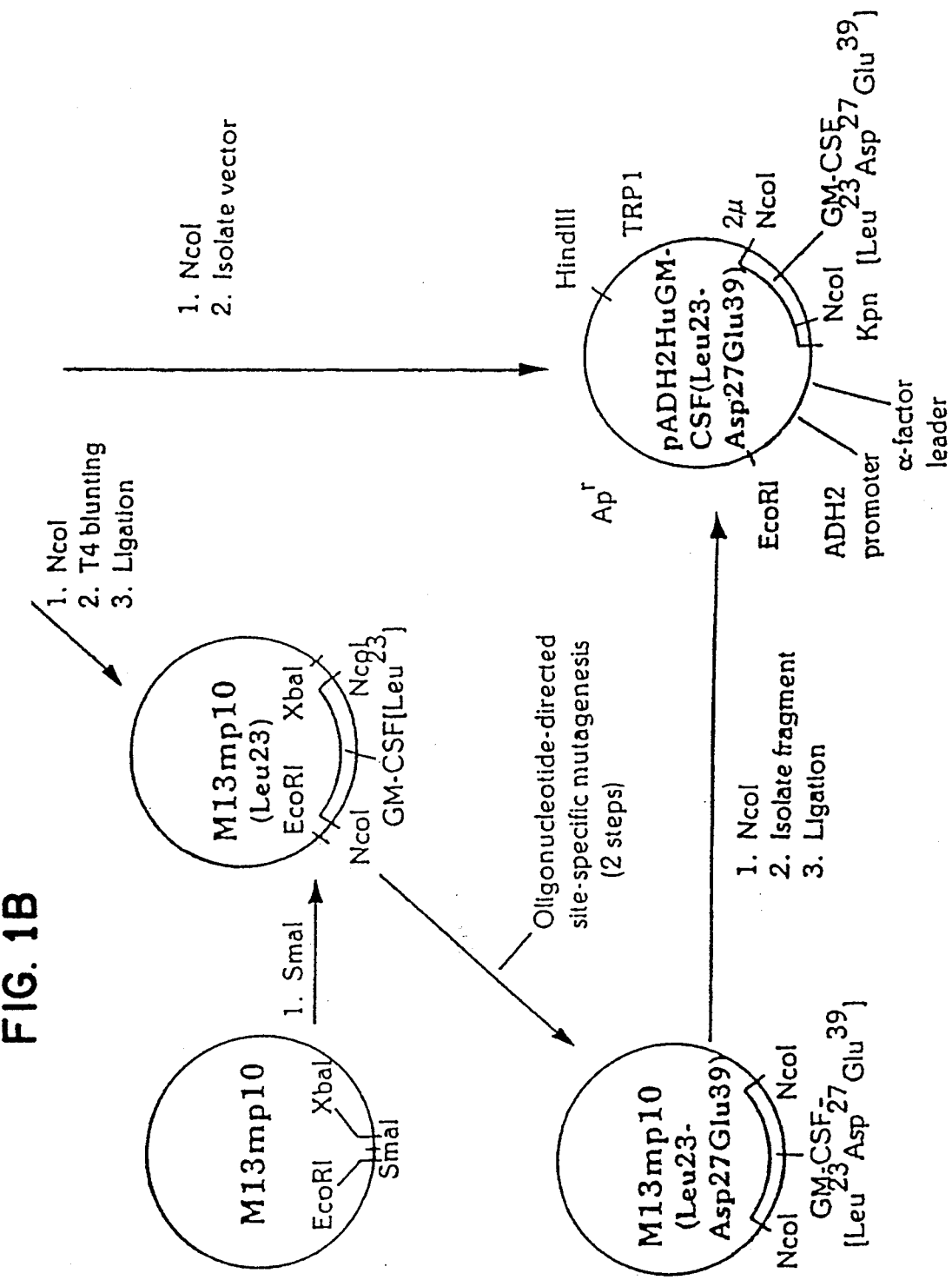

The present invention resides in the discovery that functional analogs of normally N-glycosylated immunoregulatory proteins can be translated from DNA sequences altered to encode substantially homologous mutant amino acid sequences lacking N-glycosylation sites. In a preferred embodiment, the present invention provides a nonglycosylated analog of human GM-CSF, herein designated hGM-CSF[Leu$^{23}$Asp$^{27}$Glu$^{39}$]. This analog is expressed and secreted by yeast at levels several times greater than its recombinant native homologue in comparative experiments involving substantially identical expression systems. The analog is secreted as a largely homogeneous product, and exhibits a specific activity equivalent to its natural homologue.

As used throughout the specification in a generic sense, "human colony stimulating factor" or "hCSF" means an endogenous secretory protein capable of inducing growth and differentiation of hematopoeitic cells, for example, GM-CSF, G-CSF, CSF-1, and BPA. "Mutant amino acid sequence" refers to a polypeptide sequence encoded by a nucleotide sequence variant from a native sequence. "Substantially homologous," which can refer both to nucleic acid and amino acid sequences, means that a particular subject sequence, for example, a mutant sequence, varies from a reference sequence by one or more substitutions, deletions, or additions, the net effect of which do not result in an adverse functional dissimilarity between reference and subject sequences. "Native sequence" refers to an amino acid or nucleic acid sequence which is identical to a wild-type or native form of a gene or protein. "N-glycosylation site" is defined below. The term "inactivate", as used in defining the present invention, means to alter a selected N-glycosylation site to eliminate amino acid residues enabling covalent bonding of oligosaccharide moieties. "Recombinant DNA segment" refers to a DNA molecule, isolated at least once in substantially pure or essentially pure form, i.e., in a quantity enabling identification, manipulation, and recovery of the segment and its component nucleotide sequences by standard biochemical methods, for example, using a cloning vector. "Nucleotide sequence" refers to a heteropolymer of deoxyribonucleotides. "Recombinant expression system" means a combination of a suitable cloning or expression vector and a suitable host microorganism. Yeast expression systems, particularly those employing *Saccharomyces cerevisiae*, are preferred.

N-glycosylation sites in eukaryotic proteins are characterized by the amino acid triplet Asn-A$^1$-Z, where A$^1$ is any amino acid, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between A$^1$ and Z, or an amino acid other than Asn between Asn and A$^1$. Preferably, substitutions are made conservatively; i.e., the most preferred substitute amino acids are those having physicochemical characteristics resembling those of the residue to be replaced. Similarly, when a deletion or insertion strategy is adopted, the potential effect of the deletion or insertion upon biological activity should be considered.

Thus, an analog hCSF according to the present invention is a protein having a mutant amino acids sequence which is substantially homologous to the native sequence of an hCSF having at least one N-glycosylation site, wherein at least one occurrence Asn-A$^1$-Z in the native sequence has been replaced in the mutant sequence by Asn-A$^2$-Y or X-A$^2$-A$^3$, where A$^1$, A$^2$, A$^3$ and are the same or different and can be any amino acid, X is any amino acid not Asn;

Y is any amino acid not Z; and

Z is Ser or Thr.

Preferably, all occurrences of Asn-A$^1$-Z in the native sequence are replaced in the mutant sequence by Asn-A$^2$-Y or X-A$^2$-A$^3$.

Appropriately conservative substitute amino acids for Asn include Asp, Gln, Glu, Ala, Gly, Ser, and Thr, of which Asp, Gln, and Glu are preferred. Where Z is Ser, appropriate substitutes are Met, Leu, Ile, Val, Asp, Gln, Glu, or Asn; of which Met, Leu, Ile, and Val are preferred. Where Z is Thr, conservative substitutions are Val, Glu, Asp, Gln, Gly, or Ala, preferably Val, Glu, Asp or Gln.

By comparing the sequence of the protein to be altered with the sequence of a homologous protein from another species, e.g., a mouse protein, insight regarding appropriate substitutions can be gained.

This approach can be illustrated by reference to GM-CSF. The amino acid sequences of wild-type human GM-CSF and wild-type murine GM-CSF from resides 18-44 can be aligned as follows:

|  | 18 | 19 | 20 | 21 | 22 | 23 | 24 | 25 | 26 | 27 | 28 | 29 | 30 | 31 |
|---|---|---|---|---|---|---|---|---|---|---|---|---|---|---|
| Human | Ala | Ile | Gln | Glu | Ala | Arg | Arg | Leu | Leu | Asn | Leu | Ser | Arg | Asp |
| Mouse | Ala | Ile | Lys | Glu | Ala | Leu | Asn | Leu | Leu | Asp | Asp | Met | Pro | Val |

|  | 32 | 33 | 34 | 35 | 36 | 37 | 38 | 39 | 40 | 41 | 42 | 43 | 44 |
|---|---|---|---|---|---|---|---|---|---|---|---|---|---|
| Human | Thr | Ala | Ala | Glu | Met | Asn | Glu | Thr | Val | Glu | Val | Ile | Ser |
| Mouse | Thr | Leu | — | — | — | Asn | Glu | Glu | Val | Glu | Val | Val | Ser |

Thus, the most preferred substitutions of Asp for Asn at residue 27 and Glu for Thr at residue 39 provide a new sequence lacking potential N-glycosylation sites. In addition, in order to remove a multibasic amino acid sequence at residues 23 and 24, Leu can be substituted for Arg at position 23, to provide a protein less susceptible to cleavage by the yeast KEX2 protease prior to secretion.

Alternatively, Met can be substituted for Ser at position 29, and Gln could be substituted for Asn at position 37. Other conservative amino acid substitutions could be made to provide protein lacking N-glycosylation sites. Ranking substitute amino acids by order of preference for substitution at these positions provides the following table:

TABLE 1

| hGM-CSF Amino Acid Substitutions | | | | |
|---|---|---|---|---|
| Position: | 27 | 29 | 37 | 39 |
| Wild type: | Asn | Ser | Asn | Thr |
| Most preferred: | Asp | Met | Gln | Glu |
| Second Order of preference: | Glu | Leu | Glu | Asp |
|  | Gln | Ile | Asp | Gln |
|  |  | Val |  | Val |
| Third Order of preference: | Ala | Asp | Ala | Gly |
|  | Gly | Gln | Gly | Ala |
|  | Ser | Glu | Ser |  |
|  | Thr | Asn | Thr |  |

Using a similar approach, appropriate substitutions for amino acids representing potential N-glycosylation sites in other hCSFs can be identified. Thus, the amino acid sequence of human macrophage specific colony stimulating factor (M-CSF or CSF-1) contains the sequence Asn-Glu-Thr beginning at position 122 and Asn-Asn-Ser beginning at position 140. See Kawasaki et al., *Science* 230:291 (1985). Substituting Gln, Glu, or Asp for either of the Asn residues, or using a similar conservative substitution approach for replacement of Thr[124] or Set[142] would eliminate potential N-glycosylation sites. Similarly, human burst promoting activity (BPA), also known as erythroid promoting activity (EPA), contains the sequence Asn-Gln-Ser beginning at position 31 of the mature protein, and Asn-Arg-Ser beginning at position 79. See Gasson et al., *Nature* 315:768 (1985). Replacement of either Asn residues or Ser residues with appropriate substitute amino acids will provide a protein lacking N-glycosylation sites.

To effect mutations in a selected sequence, oligonucleotide-directed site-specific mutagenesis procedures are employed to provide an altered gene having particular codons altered according to the substitution, deletion, or insertion required. Bauer et al., *Gene* 37:73 (1985); Craik, *Biotechniques*, January 1985, 12–19; Smith et al., *Genetic Engineering: Principles and Methods* (Plenum Press, 1981); and U.S. Pat. No. 4,518,584; disclose suitable techniques, and are incorporated by reference herein. According to this process, a strand, of the gene to be altered is cloned into an M13 single-stranded phage or other appropriate vector to provide a suitable quantity of single-stranded DNA comprising either the sense or antisense strand corresponding to the gene to be altered. This DNA is annealed to a fragment of M13 phage to provide a gapped duplex, which is then hybridized to an oligonucleotide primer. The primer is complementary to the sequence surrounding the codon to be altered, but comprises a codon (or an antisense codon complementary to such codon) specifying the new amino acid at the point where substitution is to be effected. If a deletion is desired, the primer will lack the particular codon specifying the amino acid to be deleted, while maintaining the correct reading frame. If an insertion is desired, the primer will include a new codon, at the appropriate location in the sequence, specifying the amino acid to be inserted. Preferably, the substitute codon, deleted codon, or inserted codon is located at or near the center of the oligonucleotide.

The size of the oligonucleotide primer employed is determined by the need to optimize stable, unique hybridization at the mutation site with the 5' and 3' extensions being of sufficient length to avoid editing of the mutation by the exonuclease activity of the DNA polymerase employed to fill gaps. Thus, oligonucleotides used in accordance with the present invention will usually contain from about 15 to about 25 bases. Oligonucleotides of greater size are not needed and are more difficult to synthesize. Conventional techniques for oligonucleotide synthesis are suitable, for example, the triester synthesis procedures disclosed by Sood et al., *Nucl. Acid Res.* 4:2557 (1977) and Hirose et al., *Tet. Lett.* 28:2449 (1978).

The oligonucleotide primer is then hybridized to the gapped duplex having a single-stranded template segment containing the gene to be altered. The primer is then extended along the template strand by reaction with DNA polymerase I (Klenow fragment), T4 DNA polymerase, or other suitable DNA polymerase. The resulting double stranded DNA is then converted to closed circular DNA by treatment with a DNA ligase, for example, T4 DNA ligase, and the resulting heteroduplex employed to transfect a suitable host strain, for example *E. coli* JM105 (Bethesda Research Laboratories). Replication of the heteroduplex by the host provides progeny of both strands. The transfected cells are then plated to provide plaques, which are screened using a labelled oligonucleotide corresponding to that used in the mutagenesis procedure. Conditions are employed which result in preferential hybridization of the primer to the mutated DNA but not to the progeny of the parent strand. DNA containing the mutated gene is then isolated and spliced into a suitable expression vector, and the vector employed to transform a host strain. The host strain is then grown in culture to provide the analog protein.

As noted previously, yeast: is preferred for expression of the analog form of recombinant human GM-CSF. Appropriate expression vectors include pYαfHuGM (ATCC 53157), which bears the wild-type human GM-CSF gene, and others known to those skilled in the art. Selection of appropriate yeast strains for transformation will be determined by the nature of the selectable markers and other features of the vector. Appropriate *S. cerevisiae* strains for transformation by pYαHuGM, and various constructions derived from that vector, include strains X2181-1B, available from the Yeast Genetic Stock Center, Berkeley, CA, USA [see below], having the genotype α trp1 gal1 ade1 his2;J17 (ATCC 52683; α his2 ade1 trp1 met14 ura3); and IL166-5B (ATCC 46183; α his1 trp1).

Additional details regarding basic recombinant DNA techniques, assays for GM-CSF activity, and growth of yeast strains are provided in copending U.S. patent application Ser. Nos. 763,130, filed Aug. 6, 1985, and 750,401, filed Jul. 2, 1985.

The following example is intended to provide additional detail regarding particular aspects of the present invention.

EXAMPLE 1

Mutagenesis of hGM-CSF[Leu[23]]

The wild-type gene coding for human GM-CSF, resident on plasmid pHG23, has been deposited with the American Type Culture Collection (ATCC), 12301 Parklawn Drive, Rockville, Md. 20852, USA, under accession number 39900. The wild-type gene inserted in a yeast expression vector, pYαfHuGM (also known as pYαfGM-2), has been deposited with the ATCC under accession number 53157. Plasmid pYαfHuGM contains DNA sequences from pBR322 for selection and replication in *E. coli* (Ap[r] gene and origin of replication) and yeast DNA sequences including an α-factor promoter, the Trp1 gene as a selectable marker and the 2μ origin of replication. Adjacent to the promoter is the α-factor leader sequence enabling secretion of heterologous proteins from a yeast host. The α-factor leader sequence is modified to contain, at its 3' end, a second KEX2 cleavage site to allow complete processing of secreted protein, as described by Brake et al., *Proc. Natl. Acad. Sci. USA* 81:4642 (1984). Details regarding the construction of the deposited plasmids are provided in copending U.S. patent applications Ser. Nos. 750,401 and 763,130, the disclosures of which are incorporated by reference herein.

A 417 base pair AhaII-NcoI fragment containing the majority of the coding region and part of the 3' flanking region of the wild-type human GM-CSF gene was excised from the pYαfHuGM plasmid to provide a fragment lacking the sequence corresponding to the first 24 amino acids of the mature protein. This portion of the gene was reconstituted using a synthesized oligonucleotide linker fragment which provides a 5' nucleotide sequence encoding an amino acid sequence coincident with the first 22 amino acids of the mature protein, but containing a 5' KpnI terminal restriction site, a BglII site at amino acid codon 4, a second NcoI site at amino acid codon 12, HpaI and HindIII sites at codons 16 and 21, respectively, and a codon substitution to provide a leucine residue at position 23. The sequence of the linker appears below:

```
                              Ala  Pro  Ala  Arg  Ser  Pro
      5'-CT TTG GAT AAA AGA GCT CCA GCT AGA TCT CCA
      3'-CAT GGA AAC CTA TTT TCT CGA GGT CGA TCT AGA GGT
         KpnI                                    BglII

Ser  Pro  Ser  Thr  Glu  Pro  Trp  Glu  His  Val  Asn  Ala  Ile
TCT CCA TCT ACT CAA CCA TGG GAA CAC GTT AAC GCT ATT
AGA GGT AGA TGA GTT GGT ACC CTT GTG CAA TTG CGA TAA
                         NcoI                HpaI

Glu  Glu  Ala  Leu
CAA GAA GCT TTG-3'
GTT CTT CGA AAC GC-5'
     HindIII       AhaII—>
```

As detailed in copending U.S. application Ser. No. 763,130, substitution of leucine for arginine at position 23 results in enhanced expression due to elimination of a yeast KEX2 protease cleavage site. The resulting construct was cloned into KpnI and NcoI-cut plasmid pBC11 to generate plasmid pBC25, which was used to transform an appropriate host strain to provide a quantity of DNA containing the modified GM-CSF gene. This plasmid is a *S. cerevisiae* expression vector substantially similar to pYαfHuGM, except for substitution of the glucose-repressible alcohol dehydrogenase 2 (ADH2) promoter for the α-factor promoter of pYαfHuGM. Alternative expression plasmids, e.g, pYαfHuGM (ATCC 53157), could be employed with equivalent success.

Plasmid DNA was isolated by conventional techniques and digested with NcoI to provide a 503 base pair fragment extending from amino acid codon 12 through 127, plus an additional 111 noncoding base pairs at the 3' end of the fragment.

This fragment was flush-ended with T4 DNA polymerase and ligated into SmaI cut M13mp10 (Amersham, Arlington Heights, Ill., USA), such that the internal HindIII site of the pBC25 fragment was proximal to the HindIII site of the M13mp10 vector. The resulting vector was employed to transfect a appropriate strain of *E. coli*, e.g., JM103, to provide bacteria actively excreting single-stranded DNA, which is isolated from the culture supernatant by conventional means.

The single-stranded DNA was then annealed to M13mp18 DNA and the following mutagenic oligonucleotide, which provides a codon substitution capable of inserting a glutamic acid (Glu) residue for threonine (Thr) at position 39:

5'-GAT GAA TGA AGA AGT AGA AGTC-3'.

After detecting and isolating the successfully mutagenized gene, designated hGM-CSF[Leu$^{23}$Glu$^{39}$], double stranded DNA containing the gene was cut with EcoR1 plus XbaI and religated into M13MP10 digested with EcoR1 and XbaI. Single stranded DNA was prepared as previously described and used in a mutagenesis reaction-employing the following mutagenic oligonucleotide, which alters the coding sequence to substitute aspartic acid (Asp) for asparagine (Asn) at position 27:

5'-CGT CTC CTG GAC CTG AGT A-3'.

After detecting and isolating the mutagenized strand, now designated hGM-CSF[Leu$^{23}$Asp$^{27}$Glu$^{39}$], double stranded DNA containing the gene was prepared, cut with NcoI, and the 503 base pair fragment religated into NcoI cut pBC25. The resulting plasmid, designated pαADH2HuGMCSFLeu23Asp27Glu39 (L207-5), has been deposited (in *E. coli* strain RR1) with the American Type Culture Collection Rockville, Md., on Oct. 8, 1986, in accordance with the Budapest Treaty for the deposit of microorganisms, under accession number 67,231.

Plasmid pαADH2HuGMCSFLeu23Asp27Glu39 was used to transform yeast strain XV2181. XV2181 is a diploid formed by mating two haploid strains, X2181-1B, available from the Yeast Genetic Stock Center, Department of Biophysics and Medical Physics, University of California, Berkeley, Calif. 94702, USA; and XV617-1-3B, available from the Department of USA Genetics, University of Washington, Seattle, Wash., USA) The transformation protocol employed was substantially similar to that described by Hinnen, et al., *Proc. Natl. Acad. Sci. USA* 75:1929 (1978), selecting for Trp+ transformants in a selective medium consisting of 0.67% yeast nitrogen base, 0.5% casamino acids, 2% glucose, 10 μg/ml adenine and 20 μ/ml uracil.

Transformed yeast were grown in 25–50 ml of rich medium (1% yeast extract, 2% peptone, and 1% glucose supplemented with 80 μg/ml adenine and 80 μg/ml uracil) at 30° C. After removing yeast by centrifugation, the resulting conditioned medium was prepared for assay by filtering through a 0.45μ cellulose acetate filter. Larger scale fermentations were conducted in a 10 liter fermenter from which cells were removed by a filtration system.

Yeast supernatants from shake flask experiments were assayed by an "immuno-dot blot" assay using αHuGM-CSF [Leu$^{23}$] antibody, substantially as described by Urdal et al., *Proc. Natl. Acad. Sci. USA* 81:6481 (1984) and Conlon et al., *J. Immunol.* 135:328 (1985), with the following variations. One μl aliquots of serially diluted yeast supernatants in phosphate buffered saline (PBS) were spotted onto an nitrocellulose filter alongside serial dilutions of homogenous preparations of purified recombinant GM-CSF. The filter was air dried and placed in "blocking" buffer consisting of 3% bovine serum albumin (BSA) in PBS for one hour, then sequentially exposed to mouse anti human GM-CSF antibody, goat anti-mouse IgG conjugated to horseradish peroxidase and a 4-chloro-1-napthol color developing solution (the latter reagents available from Biorad Laboratories, Richmond, Calif., USA), substantially according to the procedure of Burnette, *Anal. Biochem.* 112:195 (1981).

The results of the immuno-dot blot assays indicated that the new GM-CSF form was present in the yeast supernatants at a concentration oft approximately 20–40 μg/ml.

This result was confirmed in a human bone marrow proliferation assay, which measures the ability of a sample to induce differentiation and proliferation of immature bone marrow cells into granulocyte, macrophage, or mixed colonies. The results of the proliferation assays indicated that more than $50 \times 10^6$ U/ml GM-CSF activity was present in the supernatants of cultures expressing the reduced-carbohydrate form of GM-CSF. By comparison, cultures expressing the $Leu^{23}$ version, lacking modified N-glycosylation sites, provided 15–30 μg/ml by dot-blot assay and about $5$–$10 \times 10^6$ U/ml by proliferation assay.

A second expression experiment was undertaken on a larger scale. A ten liter fermenter culture of yeast harboring the pαADH2HuGMCSFLeu23Asp27Glu39 expression plasmid was conducted substantially similarly to a series of baseline fermentations involving the $Leu^{23}$ analog. Immuno-dot blot and proliferation assays indicated a yield for the nonglycosylated analog of 50–100 μg/ml rGM-CSF, versus an average of 15 μg/ml for the baseline studies.

The bulk of the material, resulting from the large-scale fermentation was purified by two sequential, reversed-phase HPLC steps on a Waters preparative HPLC column, substantially as described by Urdal et al., *J. Chromatog.* 296:171 (1984).

Briefly, yeast broth containing rGM-CSF was filtered through a 0.45μ filter and pumped, at a flow rate of 100 ml/min, onto a 5 cm×30 cm column packed with 15–20μ C-4 reversed phase silica (Vydac, the Separations Group, Hesperia, Calif., USA). The column was equilibrated in 0.1% trifluoroacetic acid in water (Solvent A) prior to the application of the yeast broth and was flushed with this solvent following application of the broth to the column until the optical absorbance of the effluent approached baseline values. At this time, a gradient of 0.1% trifluoroacetic acid in acetonitrile (Solvent B) was established that led from 0% to 100% Solvent B at a rate of change of 2% per minute and at a flow rate of 100 ml/min. Twenty minutes following initiation of the gradient, one minute fractions were collected and aliquots of the fractions analyzed for protein content by polyacrylamide gel electrophoresis and fluorescamine protein determination. Fractions containing GM-CSF from this run were pooled and then diluted with 2 volumes of 0.9M acetic acid, 0.2M pyridine, pH 4.0. The diluted pool was then pumped onto a second 5 cm×30 cm column packed with 15–20μ silica (Vydac) that had been equilibrated in 75% Solvent A2 (0.9M acetic acid, 0.2M pyridine, pH 4.0) and 25% Solvent B2 (60% n-propanol in 0.9M acetic acid, 0.2M pyridine, pH 4.5). Following application of the material, the column was flushed with additional equilibration solvent and then a gradient leading from 25% to 100% Solvent B2 was established at a rate of change of 1% solvent B2 per minute in order to elute the analog rGM-CSF from the column.

Fluorescamine protein analysis of fractions containing rGM-CSF indicated a yield of 610 mg from 8.74 l of sample, or about 69.8 μg/ml. Individual fractions from across the peak, when diluted to 1 μg/ml concentration and assayed in the proliferation assay, showed activity equivalent to that of the $Leu^{23}$ analog at the same protein concentration. This indicated that the new analog retained wild-type levels of biological activity. The level of production (about 70 μg/ml) confirmed the initial observation of an approximate five-fold increase in expression.

What is claimed is:

1. A DNA molecule encoding an analog human granulocyte macrophage colony stimulating factor that displays biological activity in a human bone marrow proliferation assay and comprises the amino acid sequence Ala Pro Ala Arg Ser Pro Ser Pro Ser Thr Gln
Pro Trp Glu His Val Asn Ala Ile Gln Glu Ala
Leu Arg Leu Leu Asp Leu Ser Arg Asp Thr Ala
Ala Glu Met Asn Glu Glu Val Glu Val Ile Ser
Glu Met Phe Asp Leu Gln Glu Pro Thr Cys Leu
Gln Thr Arg Leu Glu Leu Tyr Lys Gln Gly Leu
Arg Gly Ser Leu Thr Lys Leu Lys Gly Pro Leu
Thr Met Met Ala Ser His Tyr Lys Gln His Cys
Pro Pro Thr Pro Glu Thr Ser Cys Ala Thr Gln
Ile Ile Thr Phe Glu Ser Phe Lys Glu Asn Leu
Lys Asp Phe Leu Leu Val Ile Pro Phe Asp Cys
Trp Lys Pro Val Gln Glu.

* * * * *